(12) United States Patent
Thompson

(10) Patent No.: US 12,584,129 B1
(45) Date of Patent: Mar. 24, 2026

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 19/187,712

(22) Filed: Apr. 23, 2025

Related U.S. Application Data

(63) Continuation of application No. 18/891,208, filed on Sep. 20, 2024, now Pat. No. 12,486,506.

(51) Int. Cl.
*C12N 15/117* (2010.01)
*C12N 15/113* (2010.01)
*C12N 15/86* (2006.01)

(52) U.S. Cl.
CPC ............ *C12N 15/113* (2013.01); *C12N 15/86* (2013.01); *C12N 2310/141* (2013.01); *C12N 2710/22043* (2013.01); *C12N 2730/10143* (2013.01); *C12N 2750/14143* (2013.01)

(58) Field of Classification Search
CPC .................................................. C12N 15/113
See application file for complete search history.

(56) References Cited

U.S. PATENT DOCUMENTS

| | | | | |
|---|---|---|---|---|
| 11,085,055 | B2 * | 8/2021 | Mallol Dominguez | ..................... C12N 15/111 |
| 11,162,102 | B2 | 11/2021 | Minshull | |
| 11,530,423 | B1 | 12/2022 | Thompson | |
| 11,873,505 | B2 | 1/2024 | Thompson | |
| 12,018,274 | B2 | 6/2024 | Thompson | |
| 12,134,770 | B1 | 11/2024 | Thompson | |
| 2024/0026377 | A1 | 1/2024 | Thompson | |

FOREIGN PATENT DOCUMENTS

| | | | |
|---|---|---|---|
| CA | 2721333 | A1 | 10/2009 |

OTHER PUBLICATIONS

*Homo sapiens* C-X-C motif chemokine receptor 2 (CXCR2), transcript variant 2, mRNA. NCBI Reference Sequence: NM_001168298. 2. Jul. 15, 2024. (Year: 2024).*

*Homo sapiens* C-X-C motif chemokine receptor 2 (CXCR2), transcript variant 1, mRNA. NCBI Reference Sequence: NM_001557.4. Jul. 15, 2024. (Year: 2024).*

Korbecki et al. CXCR2 Receptor: Regulation of Expression, Signal Transduction, and Involvement in Cancer. Int. J. Mol. Sci. 2022, 23(4), 2168. (Year: 2022).*

Lundstrom. Viral Vectors in Gene Therapy: Where Do We Stand in 2023?. Lundstrom K., Viruses. Mar. 7, 2023;15(3):698). (Year: 2023).*

Kenji and Mizukami < star-protocols.cell.com/protocols/3185 >, Dec. 15, 2023, 17 pages, accessed on Oct. 3, 2025. (Year: 2023).*

Jun Zou, Anthony K. Redmond, Zhitao Qi, Helen Dooley, Chris J. Secombes, The CXC chemokine receptors of fish: Insights into CXCR evolution in the vertebrates, General and Comparative Endocrinology, vol. 215, 2015, pp. 117-131, ISSN 0016-6480, https://doi.org/10.1016/j.ygcen.2015.01.004. (Year: 2015).

Shen, P.-f., Chen, X.-q., Liao, Y.-c., Chen, N., Zhou, Q., Wei, Q., Li, X., Wang, J. and Zeng, H. (2014), MicroRNA-494-3p targets CXCR4 to suppress the proliferation, invasion, and migration of prostate cancer. Prostate, 74: 756-767. (Year: 2014).

O'Brien et al. Overview of MicroRNA Biogenesis, Mechanisms of Actions, and Circulation. Frontiers in Endocrinology, vol. 9, Article 402: 1-12 (2018) (Year: 2018).

Zhang et al. The Risks of miRNA Therapeutics: In a Drug Target Perspective. Drug Design, Development and Therapy 15: 721-733 (2021) (Year: 2021).

Ha et al. Interspecies Regulation of MicroRNAs and Their Targets. Biochim Biophys Acta. Nov. 2008; 1779(11): 735-742 (Year: 2008).

Stadtmann and Zarbock. CXCR2: from bench to bedside. Front Immunol. Aug. 24, 2012;3:263. doi: 10.3389/fimmu.2012.00263 (Year: 2012).

Lam et al. 2015. siRNA Versus miRNA as Therapeutics for Gene Silencing. Molec. Ther. Nuc. Ac. 4:e252. doi: 10.1038/mtna.2015. 23. (Year: 2015).

(Continued)

*Primary Examiner* — Neil P Hammell
*Assistant Examiner* — Amanda M Zahorik
(74) *Attorney, Agent, or Firm* — Gowling WLG (Canada) LLP

(57) ABSTRACT

The embodiments of the present disclosure relate to one or more compositions or methods that upregulate the production of one or more sequences of micro-interfering ribonucleic acid (miRNA). The sequences of miRNA may be complimentary to a sequence of target messenger RNA (mRNA) that encodes for translation of a target biomolecule, such as CXCR2. The miRNA can cause the target mRNA to be degraded or inactivated, thereby causing a decrease in bioavailability of the target biomolecule because it is degraded or inactivated by the miRNA. Decreasing the bioavailability of the target biomolecule within a subject that is administered the one or more compositions may address the afflictions experienced by the subject due to expression of the target biomolecule.

2 Claims, No Drawings
Specification includes a Sequence Listing.

(56)          References Cited

OTHER PUBLICATIONS

Ying et al. 2008. The MicroRNA (miRNA): Overview of the RNA Genes that Modulate Gene Function. Mol. Biotechnol. 38:257-268. doi: 10.1007/s12033-007-9013-8 (Year: 2008).

Gorski, S., Vogel, J. & Doudna, J. RNA-based recognition and targeting: sowing the seeds of specificity. Nat Rev Mol Cell Biol 18, 215-228 (2017). (Year: 2017).

Denzler R et al. Impact of MicroRNA Levels, Target-Site Complementarity, and Cooperativity on Competing Endogenous RNA-Regulated Gene Expression. Mol Cell. Nov. 3, 2016;64(3):565-579. doi: 10.1016/j.molcel.2016.09.027 (Year: 2016).

NCBI Reference Sequence: NG_052975.1. *Homo sapiens* C-X-C motif chemokine receptor 2 (CXCR2), RefSeqGene on chromosome 2. PRI Sep. 17, 2022. (Year: 2022).

Bottoni et al. "Targeting BTK through microRNA in chronic lymphocytic leukemia." Blood, The Journal of the American Society of Hematology 128.26 (2016): 3101-3112.

Christensen et al. "Recombinant adeno-associated virus-mediated microRNA delivery into the postnatal mouse brain reveals a role for miR-134 in dendritogenesis in vivo." Frontiers in neural circuits 3 (2010): 848.

Bofill-De Ros et al. "Guidelines for the optimal design of miRNA-based shRNAs." Methods 103 (2016): 157-166.

Van Den Berg et al. "Design of effective primary microRNA mimics with different basal stem conformations." Molecular Therapy Nucleic Acids 5 (2016).

Tritschler et al. "Concepts and limitations for learning developmental trajectories from single cell genomics." Development 146.12 (2019): dev170506.

Ahmadzadeh et al. "BRAF mutation in hairy cell leukemia." Oncology reviews 8.2 (2014): 253.

Patton et al. "Biogenesis, delivery, and function of extracellular RNA." Journal of extracellular vesicles 4.1 (2015): 27494.

Clark et al. "Detection of BRAF splicing variants in plasma-derived cell-free nucleic acids and extracellular vesicles of melanoma patients failing targeted therapy therapies." Oncotarget 11.44 (2020): 4016.

Wang et al. "Adeno-associated virus vector as a platform for gene therapy delivery." Nature reviews Drug discovery 18.5 (2019): 358-378.

Kondratov et al. "Direct head-to-head evaluation of recombinant adeno-associated viral vectors manufactured in human versus insect cells." Molecular Therapy 25.12 (2017): 2661-2675.

Nature (2010. Gene Expression. Scitable. Available online at Nature.com) <https://www.nature.com/scitable/topicpage/gene-expression-14121669> (2010).

Brutons Tyrosine Kinase Genbank Sequence (2023).

GenBank EGFR Sequence (2023).

GenBank EGF Sequence (2023).

NCBI search results for SEQ ID No. 5 (2024).

NCBI Nucleotide Sequence ALK Lingand, search performed Dec. 26, 2024 (2023).

NCBI Nucleotide Sequence ALK Receptor, search performed Dec. 26, 2024 (2023).

NCBI Nucleotide Sequence for PARP, search performed Dec. 26, 2024 (2024).

GenBank FLT3 Sequence (2024).

* cited by examiner

COMPOSITION FOR REGULATING PRODUCTION OF INTERFERING RIBONUCLEIC ACID

CROSS-REFERENCE TO RELATED APPLICATION

This application is a continuation of U.S. patent application Ser. No. 18/891,208 filed on Sep. 20, 2024, which is herein incorporated by reference.

SEQUENCE LISTING

This application contains a Sequence Listing electronically submitted via Patent Center to the United States Patent and Trademark Office as an XML Document file entitled "G10043798P5US-SequenceListing.xml" created on 2025 Aug. 5 and having a size of 16,344 bytes. The information contained in the Sequence Listing is incorporated by reference herein.

TECHNICAL FIELD

The present disclosure generally relates to compositions for regulating production of micro-interfering ribonucleic acid (miRNA). In particular, the present disclosure relates to compositions for regulating gene expression and therefore, the production of miRNA that will suppress C-X-C motif chemokine receptor 2 (CXCR2) expression.

BACKGROUND

Bioactive molecules, including receptors, are necessary for the homeostatic control of biological systems.

When bioactive molecules are over-expressed or mis-expressed, homeostasis is lost, and disease is often the result.

As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro-interfering ribonucleic acid (miRNA). The sequences of miRNA may be complementary to a sequence of target messenger RNA (mRNA) that encodes for translation of a target biomolecule and the miRNA can cause the target mRNA to be degraded or inactivated, thereby causing a decrease in bioavailability of the target biomolecule within a subject that is administered the one or more compositions. In some embodiments of the present disclosure, the target biomolecule is a C-X-C motif chemokine receptor 2 (CXCR2) molecule. In some embodiments of the present disclosure, the target biomolecule participates, directly or indirectly, in one or more immune responses. For example, the target biomolecule may be a chemokine receptor molecule that is a protein, a protein-protein complex—such as a receptor ligand pair—or other type of biomolecule that directly or indirectly suppresses an immune response or that directly or indirectly stimulates an immune response.

In some embodiments of the present disclosure the compositions comprise a plasmid of deoxyribonucleic acid (DNA) that includes one or more insert sequences of nucleotides that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a composition that comprises a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets mRNA of C-X-C motif chemokine receptor 2 (CXCR2).

Some embodiments of the present disclosure relate to a method of making a composition/target cell complex. The method comprising a step of administering a RP comprising SEQ ID NO. 1 and SEQ ID NO. 2 to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence mRNA of a target biomolecule, for example CXCR2. A first approach utilizes gene vectors containing nucleotide sequences for increasing the endogenous production of one or more sequences of miRNA, which are complete or partial sequences and/or combinations thereof, that target and silence the mRNA of CXCR2, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a C-X-C motif chemokine receptor that is found within a subject, such as a C-X-C motif chemokine receptor 2 (CXCR2). A biomolecule may be endogenous or exogenous to a subject and when bioavailable the biomolecule may suppress, influence or stimulate an immune process within the subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of miRNA that decreases the production of target biomolecules. The miRNA may, directly or indirectly, bind to and degrade the mRNA of the target biomolecule, also referred to as the target mRNA, or otherwise inactivate the target mRNA so that less or none of the target-biomolecule protein is produced.

In some embodiments of the present disclosure, the target biomolecule is CXCR2.

In some embodiments of the present disclosure, the insert comprises one or more nucleotide sequences that each encode one or more miRNA sequences that may be complementary to and degrade, or cause degradation and/or inactivation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complementary to and degrade, or cause degradation of, one biomolecule, such as CXCR2. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complementary to and degrade, or cause degradation of, or inactivate, or cause inactivation of, one biomolecule, such as CXCR2.

In some embodiments of the present disclosure, the delivery vehicle of the RP used for gene therapy may be a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ $TCID_{50}$/kg (50% tissue culture infective dose per kilogram of the patient's body mass. In some embodiments of the present disclosure, the therapeutically effective amount of the composition that is administered to the patient is about $1 \times 10^{13}$ $TCID_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1 \times 10^{16}$ TCP/kg.

Some embodiments of the present disclosure relate to an adenovirus associated virus (AAV) genome consisting of a RP that when operable inside a target cell will cause the target cell to produce a miRNA sequence that downregulates production of a biomolecule, with an example being CXCR2. The RP is comprised of AAV2 inverted terminal repeats (ITRs), a composite CASI promoter, a human growth hormone (HGH) signal peptide followed by a miRNA expression cassette containing up to six different miRNAs targeting CXCR2, followed by a Woodchuck Hepatitis Virus post-transcriptional regulatory element (WPRE) and an SV40 polyA signal.

SEQ ID NO. 1 (backbone sequence No. 1):

5'

TCTAGAATAATCAACCTCTGGATTACAAAATTTGTGAAAGATTGACTGGTATTCTTA

ACTATGTTGCTCCTTTTACGCTATGTGGATACGCTGCTTTAATGCCTTTGTATCATGC

TATTGCTTCCCGTATGGCTTTCATTTTCTCCTCCTTGTATAAATCCTGGTTGCTGTCTC

TTTATGAGGAGTTGTGGCCCGTTGTCAGGCAACGTGGCGTGGTGTGCACTGTGTTTG

CTGACGCAACCCCCACTGGTTGGGGCATTGCCACCACCTGTCAGCTCCTTTCCGGGA

CTTTCGCTTTCCCCCTCCCTATTGCCACGGCGGAACTCATCGCCGCCTGCCTTGCCCG

CTGCTGGACAGGGGCTCGGCTGTTGGGCACTGACAATTCCGTGGTGTTGTCGGGGAA

ATCATCGTCCTTTCCTTGGCTGCTCGCCTGTGTTGCCACCTGGATTCTGCGCGGGACG

TCCTTCTGCTACGTCCCTTCGGCCCTCAATCCAGCGGACCTTCCTTCCCGCGGCCTGC

TGCCGGCTCTGCGGCCTCTTCCGCGTCTTCGCCTTCGCCCTCAGACGAGTCGGATCTC

CCTTTGGGCCGCCTCCCCGCCTAAGCTTATCGATACCGTCGAGATCTAACTTGTTTAT

TGCAGCTTATAATGGTTACAAATAAAGCAATAGCATCACAAATTTCACAAATAAAG

-continued

CATTTTTTTCACTGCATTCTAGTTGTGGTTTGTCCAAACTCATCAATGTATCTTATCAT

GTCTGGATCTCGACCTCGACTAGAGCATGGCTACGTAGATAAGTAGCATGGCGGGTT

AATCATTAACTACAAGGAACCCCTAGTGATGGAGTTGGCCACTCCCTCTCTGCGCGC

TCGCTCGCTCACTGAGGCCGGGCGACCAAAGGTCGCCCGACGCCCGGGCTTTGCCC

GGGCGGCCTCAGTGAGCGAGCGAGCGCGCAGCTGGCGTAATAGCGAAGAGGCCCG

CACCGATCGCCCTTCCCAACAGTTGCGCAGCCTGAATGGCGAATGGCGATTCCGTTG

CAATGGCTGGCGGTAATATTGTTCTGGATATTACCAGCAAGGCCGATAGTTTGAGTT

CTTCTACTCAGGCAAGTGATGTTATTACTAATCAAAGAAGTATTGCGACAACGGTTA

ATTTGCGTGATGGACAGACTCTTTTACTCGGTGGCCTCACTGATTATAAAAACACTT

CTCAGGATTCTGGCGTACCGTTCCTGTCTAAAATCCCTTTAATCGGCCTCCTGTTTAG

CTCCCGCTCTGATTCTAACGAGGAAAGCACGTTATACGTGCTCGTCAAAGCAACCAT

AGTACGCGCCCTGTAGCGGCGCATTAAGCGCGGCGGGTGTGGTGGTTACGCGCAGC

GTGACCGCTACACTTGCCAGCGCCCTAGCGCCCGCTCCTTTCGCTTTCTTCCCTTCCT

TTCTCGCCACGTTCGCCGGCTTTCCCCGTCAAGCTCTAAATCGGGGGCTCCCTTTAGG

GTTCCGATTTAGTGCTTTACGGCACCTCGACCCCAAAAAACTTGATTAGGGTGATGG

TTCACGTAGTGGGCCATCGCCCTGATAGACGGTTTTTCGCCCTTTGACGTTGGAGTCC

ACGTTCTTTAATAGTGGACTCTTGTTCCAAACTGGAACAACACTCAACCCTATCTCG

GTCTATTCTTTTGATTTATAAGGGATTTTGCCGATTTCGGCCTATTGGTTAAAAAATG

AGCTGATTTAACAAAAATTTAACGCGAATTTTAACAAATATTAACGTTTACAATTT

AAATATTTGCTTATACAATCTTCCTGTTTTTGGGGCTTTTCTGATTATCAACCGGGGT

ACATATGATTGACATGCTAGTTTTACGATTACCGTTCATCGATTCTCTTGTTTGCTCC

AGACTCTCAGGCAATGACCTGATAGCCTTTGTAGAGACCTCTCAAAAATAGCTACCC

TCTCCGGCATGAATTTATCAGCTAGAACGGTTGAATATCATATTGATGGTGATTTGA

CTGTCTCCGGCCTTTCTCACCCGTTTGAATCTTTACCTACACATTACTCAGGCATTGC

ATTTAAAATATATGAGGGTTCTAAAAATTTTTATCCTTGCGTTGAAATAAAGGCTTCT

CCCGCAAAAGTATTACAGGGTCATAATGTTTTTGGTACAACCGATTTAGCTTTATGC

TCTGAGGCTTTATTGCTTAATTTTGCTAATTCTTTGCCTTGCCTGTATGATTTATTGGA

TGTTGGAATTCCTGATGCGGTATTTTCTCCTTACGCATCTGTGCGGTATTTCACACCG

CATATGGTGCACTCTCAGTACAATCTGCTCTGATGCCGCATAGTTAAGCCAGCCCCG

ACACCCGCCAACACCCGCTGACGCGCCCTGACGGGCTTGTCTGCTCCCGGCATCCGC

TTACAGACAAGCTGTGACCGTCTCCGGGAGCTGCATGTGTCAGAGGTTTTCACCGTC

ATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCG

CGGAACCCCTATTTGTTTATTTTTCTAAATACATTCAAATATGTATCCGCTCATGAGA

CAATAACCCTGATAAATGCTTCAATAATATTGAAAAAGGAAGAGTATGAGTATTCA

ACATTTCCGTGTCGCCCTTATTCCCTTTTTTGCGGCATTTTGCCTTCCTGTTTTTGCTC

ACCCAGAAACGCTGGTGAAAGTAAAAGATGCTGAAGATCAGTTGGGTGCACGAGTG

GGTTACATCGAACTGGATCTCAACAGCGGTAAGATCCTTGAGAGTTTTCGCCCCGAA

GAACGTTTTCCAATGATGAGCACTTTTAAAGTTCTGCTATGTGGCGCGGTATTATCCC

GTATTGACGCCGGGCAAGAGCAACTCGGTCGCCGCATACACTATTCTCAGAATGACT

TGGTTGAGTACTCACCAGTCACAGAAAAGCATCTTACGGATGGCATGACAGTAAGA

-continued

GAATTATGCAGTGCTGCCATAACCATGAGTGATAACACTGCGGCCAACTTACTTCTG

ACAACGATCGGAGGACCGAAGGAGCTAACCGCTTTTTTGCACAACATGGGGGATCA

TGTAACTCGCCTTGATCGTTGGGAACCGGAGCTGAATGAAGCCATACCAAACGACG

AGCGTGACACCACGATGCCTGTAGCAATGGCAACAACGTTGCGCAAACTATTAACT

GGCGAACTACTTACTCTAGCTTCCCGGCAACAATTAATAGACTGGATGGAGGCGGAT

AAAGTTGCAGGACCACTTCTGCGCTCGGCCCTTCCGGCTGGCTGGTTTATTGCTGAT

AAATCTGGAGCCGGTGAGCGTGGGTCTCGCGGTATCATTGCAGCACTGGGGCCAGA

TGGTAAGCCCTCCCGTATCGTAGTTATCTACACGACGGGGAGTCAGGCAACTATGGA

TGAACGAAATAGACAGATCGCTGAGATAGGTGCCTCACTGATTAAGCATTGGTAAC

TGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACG

TGAGTTTTCGTTCCACTGAGCGTCAGACCCCGTAGAAAAGATCAAAGGATCTTCTTG

AGATCCTTTTTTTCTGCGCGTAATCTGCTGCTTGCAAACAAAAAAACCACCGCTACC

AGCGGTGGTTTGTTTGCCGGATCAAGAGCTACCAACTCTTTTTCCGAAGGTAACTGG

CTTCAGCAGAGCGCAGATACCAAATACTGTCCTTCTAGTGTAGCCGTAGTTAGGCCA

CCACTTCAAGAACTCTGTAGCACCGCCTACATACCTCGCTCTGCTAATCCTGTTACC

AGTGGCTGCTGCCAGTGGCGATAAGTCGTGTCTTACCGGGTTGGACTCAAGACGATA

GTTACCGGATAAGGCGCAGCGGTCGGGCTGAACGGGGGGTTCGTGCACACAGCCCA

GCTTGGAGCGAACGACCTACACCGAACTGAGATACCTACAGCGTGAGCTATGAGAA

AGCGCCACGCTTCCCGAAGGGAGAAAGGCGGACAGGTATCCGGTAAGCGGCAGGG

TCGGAACAGGAGAGCGCACGAGGGAGCTTCCAGGGGGAAACGCCTGGTATCTTTAT

AGTCCTGTCGGGTTTCGCCACCTCTGACTTGAGCGTCGATTTTTGTGATGCTCGTCAG

GGGGGCGGAGCCTATGGAAAAACGCCAGCAACGCGGCCTTTTTACGGTTCCTGGCC

TTTTGCTGGCCTTTTGCTCACATGTTCTTTCCTGCGTTATCCCCTGATTCTGTGGATAA

CCGTATTACCGCCTTTGAGTGAGCTGATACCGCTCGCCGCAGCCGAACGACCGAGCG

CAGCGAGTCAGTGAGCGAGGAAGCGGAAGAGCGCCCAATACGCAAACCGCCTCTCC

CCGCGCGTTGGCCGATTCATTAATGCAGCAGCTGCGCGCTCGCTCGCTCACTGAGGC

CGCCCGGGCAAAGCCCGGGCGTCGGGCGACCTTTGGTCGCCCGGCCTCAGTGAGCG

AGCGAGCGCGCAGAGAGGGAGTGGCCAACTCCATCACTAGGGGTTCCTTGTAGTTA

ATGATTAACCCGCCATGCTACTTATCTACGTAGCCATGCTCTAGGACATTGATTATTG

ACTAGTGGAGTTCCGCGTTACATAACTTACGGTAAATGGCCCGCCTGGCTGACCGCC

CAACGACCCCCGCCCATTGACGTCAATAATGACGTATGTTCCCATAGTAACGCCAAT

AGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGACGGTAA

ATGGCCCGCCTGGCATTATGCCCAGTACATGACCTTATGGGACTTTCCTACTTGGCA

GTACATCTACGTATTAGTCATCGCTATTACCATGGTCGAGGTGAGCCCCACGTTCTG

CTTCACTCTCCCCATCTCCCCCCCCTCCCCACCCCCAATTTTGTATTTATTTATTTTTT

AATTATTTTGTGCAGCGATGGGGGCGGGGGGGGGGGGGGCGCGCGCCAGGCGGG

GCGGGGCGGGGCGAGGGGCGGGGCGGGGCGAGGCGGAGAGGTGCGGCGGCAGCCA

ATCAGAGCGGCGCGCTCCGAAAGTTTCCTTTTATGGCGAGGCGGCGGCGGCGGCGG

-continued

CCCTATAAAAAGCGAAGCGCGCGGCGGGCGGGAGTCGCTGCGCGCTGCCTTCGCCC

CGTGCCCCGCTCCGCCGCCGCCTCGCGCCGCCCGCCCCGGCTCTGACTGACCGCGTT

ACTAAAACAGGTAAGTCCGGCCTCCGCGCCGGGTTTTGGCGCCTCCCGCGGGCGCCC

CCCTCCTCACGGCGAGCGCTGCCACGTCAGACGAAGGGCGCAGCGAGCGTCCTGAT

CCTTCCGCCCGGACGCTCAGGACAGCGGCCCGCTGCTCATAAGACTCGGCCTTAGAA

CCCCAGTATCAGCAGAAGGACATTTTAGGACGGGACTTGGGTGACTCTAGGGCACT

GGTTTTCTTTCCAGAGAGCGGAACAGGCGAGGAAAAGTAGTCCCTTCTCGGCGATTC

TGCGGAGGGATCTCCGTGGGGCGGTGAACGCCGATGATGCCTCTACTAACCATGTTC

ATGTTTTCTTTTTTTTTCTACAGGTCCTGGGTGACGAACAGGGTACCGCCACC

3'

SEQ ID NO. 2 (miRNA expression cassette No. 2 - CXCR2):

5'

ATGGCCACCGGCTCTCGCACAAGCCTGCTGCTGGCTTTCGGACTGCTGTGCCTGCCT

TGGCTCCAGGAGGGCTCCGCCGCTAGCATCGATACCGTCGCTATGTGCTGGAGGCTT

GCTGAAGGCTGTATGCTGATAGTTGCTCATGGATCTTCGCCGTTTTGGCCTCTGACTG

ACGGCGAAGATCTGAGCAACTATCAGGACACAAGGCCTGTTACTAGCACTCACATG

GAACAAATGGCCTCTAGCCTGGAGGCTTGCTGAAGGCTGTATGCTGATGTTTCTGGC

ATCCATATGCGCGTTTTGGCCTCTGACTGACGCGCATATGGGCCAGAAACATCAGGA

CACAAGGCCTGTTACTAGCACTCACATGGAACAAATGGCCTCTAGCCTGGAGGCTTG

CTGAAGGCTGTATGCTGAGAATTTCGGTAACGCATCCAGCGTTTTGGCCTCTGACTG

ACGCTGGATGCGACCGAAATTCTCAGGACACAAGGCCTGTTACTAGCACTCACATG

GAACAAATGGCCTC

3'

SEQ ID NO: 3 = SEQ ID NO: 1 + SEQ ID NO: 2

5'

TCTAGAATAATCAACCTCTGGATTACAAAATTTGTGAAAGATTGACTGGTATTCTTA

ACTATGTTGCTCCTTTTACGCTATGTGGATACGCTGCTTTAATGCCTTTGTATCATGC

TATTGCTTCCCGTATGGCTTTCATTTTCTCCTCCTTGTATAAATCCTGGTTGCTGTCTC

TTTATGAGGAGTTGTGGCCCGTTGTCAGGCAACGTGGCGTGGTGTGCACTGTGTTTG

CTGACGCAACCCCCACTGGTTGGGGCATTGCCACCACCTGTCAGCTCCTTTCCGGGA

CTTTCGCTTTCCCCCTCCCTATTGCCACGGCGGAACTCATCGCCGCCTGCCTTGCCCG

CTGCTGGACAGGGGCTCGGCTGTTGGGCACTGACAATTCCGTGGTGTTGTCGGGGAA

ATCATCGTCCTTTCCTTGGCTGCTCGCCTGTGTTGCCACCTGGATTCTGCGCGGGACG

TCCTTCTGCTACGTCCCTTCGGCCCTCAATCCAGCGGACCTTCCTTCCCGCGGCCTGC

TGCCGGCTCTGCGGCCTCTTCCGCGTCTTCGCCTTCGCCCTCAGACGAGTCGGATCTC

CCTTTGGGCCGCCTCCCCGCCTAAGCTTATCGATACCGTCGAGATCTAACTTGTTTAT

TGCAGCTTATAATGGTTACAAATAAAGCAATAGCATCACAAATTTCACAAATAAAG

CATTTTTTTCACTGCATTCTAGTTGTGGTTTGTCCAAACTCATCAATGTATCTTATCAT

GTCTGGATCTCGACCTCGACTAGAGCATGGCTACGTAGATAAGTAGCATGGCGGGTT

AATCATTAACTACAAGGAACCCCTAGTGATGGAGTTGGCCACTCCCTCTCTGCGCGC

TCGCTCGCTCACTGAGGCCGGGCGACCAAAGGTCGCCCGACGCCCGGGCTTTGCCC

-continued

```
GGGCGGCCTCAGTGAGCGAGCGAGCGCGCAGCTGGCGTAATAGCGAAGAGGCCCG

CACCGATCGCCCTTCCCAACAGTTGCGCAGCCTGAATGGCGAATGGCGATTCCGTTG

CAATGGCTGGCGGTAATATTGTTCTGGATATTACCAGCAAGGCCGATAGTTTGAGTT

CTTCTACTCAGGCAAGTGATGTTATTACTAATCAAAGAAGTATTGCGACAACGGTTA

ATTTGCGTGATGGACAGACTCTTTTACTCGGTGGCCTCACTGATTATAAAAACACTT

CTCAGGATTCTGGCGTACCGTTCCTGTCTAAAATCCCTTTAATCGGCCTCCTGTTTAG

CTCCCGCTCTGATTCTAACGAGGAAAGCACGTTATACGTGCTCGTCAAAGCAACCAT

AGTACGCGCCCTGTAGCGGCGCATTAAGCGCGGCGGGTGTGGTGGTTACGCGCAGC

GTGACCGCTACACTTGCCAGCGCCCTAGCGCCCGCTCCTTTCGCTTTCTTCCCTTCCT

TTCTCGCCACGTTCGCCGGCTTTCCCCGTCAAGCTCTAAATCGGGGGCTCCCTTTAGG

GTTCCGATTTAGTGCTTTACGGCACCTCGACCCCAAAAAACTTGATTAGGGTGATGG

TTCACGTAGTGGGCCATCGCCCTGATAGACGGTTTTTCGCCCTTTGACGTTGGAGTCC

ACGTTCTTTAATAGTGGACTCTTGTTCCAAACTGGAACAACACTCAACCCTATCTCG

GTCTATTCTTTTGATTTATAAGGGATTTTGCCGATTTCGGCCTATTGGTTAAAAAATG

AGCTGATTTAACAAAAATTTAACGCGAATTTTAACAAAATATTAACGTTTACAATTT

AAATATTTGCTTATACAATCTTCCTGTTTTTGGGGCTTTTCTGATTATCAACCGGGGT

ACATATGATTGACATGCTAGTTTTACGATTACCGTTCATCGATTCTCTTGTTTGCTCC

AGACTCTCAGGCAATGACCTGATAGCCTTTGTAGAGACCTCTCAAAAATAGCTACCC

TCTCCGGCATGAATTTATCAGCTAGAACGGTTGAATATCATATTGATGGTGATTTGA

CTGTCTCCGGCCTTTCTCACCCGTTTGAATCTTTACCTACACATTACTCAGGCATTGC

ATTTAAAATATATGAGGGTTCTAAAAATTTTTATCCTTGCGTTGAAATAAAGGCTTCT

CCCGCAAAAGTATTACAGGGTCATAATGTTTTTGGTACAACCGATTTAGCTTTATGC

TCTGAGGCTTTATTGCTTAATTTTGCTAATTCTTTGCCTTGCCTGTATGATTTATTGGA

TGTTGGAATTCCTGATGCGGTATTTTCTCCTTACGCATCTGTGCGGTATTTCACACCG

CATATGGTGCACTCTCAGTACAATCTGCTCTGATGCCGCATAGTTAAGCCAGCCCCG

ACACCCGCCAACACCCGCTGACGCGCCCTGACGGGCTTGTCTGCTCCCGGCATCCGC

TTACAGACAAGCTGTGACCGTCTCCGGGAGCTGCATGTGTCAGAGGTTTTCACCGTC

ATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCG

CGGAACCCCTATTTGTTTATTTTTCTAAATACATTCAAATATGTATCCGCTCATGAGA

CAATAACCCTGATAAATGCTTCAATAATATTGAAAAAGGAAGAGTATGAGTATTCA

ACATTTCCGTGTCGCCCTTATTCCCTTTTTTGCGGCATTTTGCCTTCCTGTTTTTGCTC

ACCCAGAAACGCTGGTGAAAGTAAAAGATGCTGAAGATCAGTTGGGTGCACGAGTG

GGTTACATCGAACTGGATCTCAACAGCGGTAAGATCCTTGAGAGTTTTCGCCCCGAA

GAACGTTTTCCAATGATGAGCACTTTTAAAGTTCTGCTATGTGGCGCGGTATTATCCC

GTATTGACGCCGGGCAAGAGCAACTCGGTCGCCGCATACACTATTCTCAGAATGACT

TGGTTGAGTACTCACCAGTCACAGAAAAGCATCTTACGGATGGCATGACAGTAAGA

GAATTATGCAGTGCTGCCATAACCATGAGTGATAACACTGCGGCCAACTTACTTCTG

ACAACGATCGGAGGACCGAAGGAGCTAACCGCTTTTTTGCACAACATGGGGGATCA

TGTAACTCGCCTTGATCGTTGGGAACCGGAGCTGAATGAAGCCATACCAAACGACG
```

-continued

```
AGCGTGACACCACGATGCCTGTAGCAATGGCAACAACGTTGCGCAAACTATTAACT

GGCGAACTACTTACTCTAGCTTCCCGGCAACAATTAATAGACTGGATGGAGGCGGAT

AAAGTTGCAGGACCACTTCTGCGCTCGGCCCTTCCGGCTGGCTGGTTTATTGCTGAT

AAATCTGGAGCCGGTGAGCGTGGGTCTCGCGGTATCATTGCAGCACTGGGGCCAGA

TGGTAAGCCCTCCCGTATCGTAGTTATCTACACGACGGGGAGTCAGGCAACTATGGA

TGAACGAAATAGACAGATCGCTGAGATAGGTGCCTCACTGATTAAGCATTGGTAAC

TGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACG

TGAGTTTTCGTTCCACTGAGCGTCAGACCCCGTAGAAAAGATCAAAGGATCTTCTTG

AGATCCTTTTTTTCTGCGCGTAATCTGCTGCTTGCAAACAAAAAAACCACCGCTACC

AGCGGTGGTTTGTTTGCCGGATCAAGAGCTACCAACTCTTTTTCCGAAGGTAACTGG

CTTCAGCAGAGCGCAGATACCAAATACTGTCCTTCTAGTGTAGCCGTAGTTAGGCCA

CCACTTCAAGAACTCTGTAGCACCGCCTACATACCTCGCTCTGCTAATCCTGTTACC

AGTGGCTGCTGCCAGTGGCGATAAGTCGTGTCTTACCGGGTTGGACTCAAGACGATA

GTTACCGGATAAGGCGCAGCGGTCGGGCTGAACGGGGGGTTCGTGCACACAGCCCA

GCTTGGAGCGAACGACCTACACCGAACTGAGATACCTACAGCGTGAGCTATGAGAA

AGCGCCACGCTTCCCGAAGGGAGAAAGGCGGACAGGTATCCGGTAAGCGGCAGGG

TCGGAACAGGAGAGCGCACGAGGGAGCTTCCAGGGGGAAACGCCTGGTATCTTTAT

AGTCCTGTCGGGTTTCGCCACCTCTGACTTGAGCGTCGATTTTTGTGATGCTCGTCAG

GGGGGCGGAGCCTATGGAAAAACGCCAGCAACGCGGCCTTTTTACGGTTCCTGGCC

TTTTGCTGGCCTTTTGCTCACATGTTCTTTCCTGCGTTATCCCCTGATTCTGTGGATAA

CCGTATTACCGCCTTTGAGTGAGCTGATACCGCTCGCCGCAGCCGAACGACCGAGCG

CAGCGAGTCAGTGAGCGAGGAAGCGGAAGAGCGCCCAATACGCAAACCGCCTCTCC

CCGCGCGTTGGCCGATTCATTAATGCAGCAGCTGCGCGCTCGCTCGCTCACTGAGGC

CGCCCGGGCAAAGCCCGGGCGTCGGGCGACCTTTGGTCGCCCGGCCTCAGTGAGCG

AGCGAGCGCGCAGAGAGGGAGTGGCCAACTCCATCACTAGGGGTTCCTTGTAGTTA

ATGATTAACCCGCCATGCTACTTATCTACGTAGCCATGCTCTAGGACATTGATTATTG

ACTAGTGGAGTTCCGCGTTACATAACTTACGGTAAATGGCCCGCCTGGCTGACCGCC

CAACGACCCCCGCCCATTGACGTCAATAATGACGTATGTTCCCATAGTAACGCCAAT

AGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGACGGTAA

ATGGCCCGCCTGGCATTATGCCCAGTACATGACCTTATGGGACTTTCCTACTTGGCA

GTACATCTACGTATTAGTCATCGCTATTACCATGGTCGAGGTGAGCCCCACGTTCTG

CTTCACTCTCCCCATCTCCCCCCCCTCCCCACCCCCAATTTTGTATTTATTTATTTTTT

AATTATTTTGTGCAGCGATGGGGGCGGGGGGGGGGGGGGCGCGCGCCAGGCGGG

GCGGGGCGGGGCGAGGGGCGGGGCGGGGCGAGGCGGAGAGGTGCGGCGGCAGCCA

ATCAGAGCGGCGCGCTCCGAAAGTTTCCTTTTATGGCGAGGCGGCGGCGGCGGCGG

CCCTATAAAAAGCGAAGCGCGCGGCGGGCGGGAGTCGCTGCGCGCTGCCTTCGCCC

CGTGCCCCGCTCCGCCGCCGCCTCGCGCCGCCCGCCCCGGCTCTGACTGACCGCGTT

ACTAAAACAGGTAAGTCCGGCCTCCGCGCCGGGTTTTGGCGCCTCCCGCGGGCGCCC

CCCTCCTCACGGCGAGCGCTGCCACGTCAGACGAAGGGCGCAGCGAGCGTCCTGAT
```

-continued

CCTTCCGCCCGGACGCTCAGGACAGCGGCCCGCTGCTCATAAGACTCGGCCTTAGAA

CCCCAGTATCAGCAGAAGGACATTTTAGGACGGGACTTGGGTGACTCTAGGGCACT

GGTTTTCTTTCCAGAGAGCGGAACAGGCGAGGAAAAGTAGTCCCTTCTCGGCGATTC

TGCGGAGGGATCTCCGTGGGGCGGTGAACGCCGATGATGCCTCTACTAACCATGTTC

ATGTTTTCTTTTTTTTTCTACAGGTCCTGGGTGACGAACAGGGTACCGCCACCATGGC

CACCGGCTCTCGCACAAGCCTGCTGCTGGCTTTCGGACTGCTGTGCCTGCCTTGGCT

CCAGGAGGGCTCCGCCGCTAGCATCGATACCGTCGCTATGTGCTGGAGGCTTGCTGA

AGGCTGTATGCTGATAGTTGCTCATGGATCTTCGCCGTTTTGGCCTCTGACTGACGGC

GAAGATCTGAGCAACTATCAGGACACAAGGCCTGTTACTAGCACTCACATGGAACA

AATGGCCTCTAGCCTGGAGGCTTGCTGAAGGCTGTATGCTGATGTTTCTGGCATCCA

TATGCGCGTTTTGGCCTCTGACTGACGCGCATATGGGCCAGAAACATCAGGACACAA

GGCCTGTTACTAGCACTCACATGGAACAAATGGCCTCTAGCCTGGAGGCTTGCTGAA

GGCTGTATGCTGAGAATTTCGGTAACGCATCCAGCGTTTTGGCCTCTGACTGACGCT

GGATGCGACCGAAATTCTCAGGACACAAGGCCTGTTACTAGCACTCACATGGAACA

AATGGCCTC

3'

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 3, or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes are integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. A composition that comprises a recombinant plasmid (RP) that comprises a sequence of nucleotides that is 100% identical to the full length of SEQ ID NO: 3.

2. The composition of claim 1, wherein the RP is encapsulated in a protein coat, a lipid vesicle, or any combination thereof.

* * * * *

SEQUENCE LISTING

```
Sequence total quantity: 3
SEQ ID NO: 1            moltype = DNA  length = 5813
FEATURE                 Location/Qualifiers
source                  1..5813
                        mol_type = other DNA
                        organism = synthetic construct
SEQUENCE: 1
tctagaataa tcaacctctg gattacaaaa tttgtgaaag attgactggt attcttaact  60
atgttgctcc ttttacgcta tgtggatacg ctgctttaat gcctttgtat catgctattg  120
cttcccgtat ggctttcatt ttctcctcct tgtataaatc ctggttgctg tctctttatg  180
aggagttgtg gcccgttgtc aggcaacgtg gcgtggtgtg cactgtgttt gctgacgcaa  240
```

-continued

```
cccccactgg ttggggcatt gccaccacct gtcagctcct ttccgggact ttcgctttcc   300
ccctccctat tgccacggcg gaactcatcg ccgcctgcct tgcccgctgc tggacagggg   360
ctcggctgtt gggcactgac aattccgtgg tgttgtcggg gaaatcatcg tcctttcctt   420
ggctgctcgc ctgtgttgcc acctggattc tgcgcgggac gtccttctgc tacgtccctt   480
cggccctcaa tccagcggac cttccttccc gcggcctgct gccggctctg cggcctcttc   540
cgcgtcttcg ccttcgccct cagacgagtc ggatctccct ttgggccgcc tccccgccta   600
agcttatcga taccgtcgag atctaacttg tttattgcag cttataatgg ttacaaataa   660
agcaatagca tcacaaattt cacaaataaa gcattttttt cactgcattc tagttgtggt   720
ttgtccaaac tcatcaatgt atcttatcat gtctggatct cgacctcgac tagagcatgg   780
ctacgtagat aagtagcatg gcgggttaat cattaactac aaggaacccc tagtgatgga   840
gttggccact ccctctctgc gcgctcgctc gctcactgag gccgggcgac caaaggtcgc   900
ccgacgcccg ggctttgccc gggcggcctc agtgagcgag cgagcgcgca gctggcgtaa   960
tagcgaagag gcccgcaccg atcgcccttc ccaacagttg cgcagcctga atggcgaatg  1020
gcgattccgt tgcaatggct ggcggtaata ttgttctgga tattaccagc aaggccgata  1080
gtttgagttc ttctactcag gcaagtgatg ttattactaa tcaaagaagt attgcgacaa  1140
cggttaattt gcgtgatgga cagactcttt tactcggtgg cctcactgat tataaaaaca  1200
cttctcagga ttctggcgta ccgttcctgt ctaaaatccc tttaatcggc ctcctgttta  1260
gctcccgctc tgattctaac gaggaaagca cgttatacgt gctcgtcaaa gcaaccatag  1320
tacgcgccct gtagcggcgc attaagcgcg gcgggtgtgg tggttacgcg cagcgtgacc  1380
gctacacttg ccagcgccct agcgcccgct cctttcgctt tcttcccttc ctttctcgcc  1440
acgttcgccg gctttccccg tcaagctcta aatcggggggc tccctttagg gttccgattt  1500
agtgctttac ggcacctcga ccccaaaaaa cttgattagg gtgatggttc acgtagtggg  1560
ccatcgccct gatagacggt ttttcgccct ttgacgttgg agtccacgtt ctttaatagt  1620
ggactcttgt tccaaactgg aacaacactc aaccctatct cggtctattc ttttgattta  1680
taagggattt tgccgatttc ggcctattgg ttaaaaaatg agctgattta acaaaaattt  1740
aacgcgaatt ttaacaaaat attaacgttt acaatttaca tatttgctta tacaatcttc  1800
ctgttttttgg ggcttttctg attatcaacc ggggtacata tgattgacat gctagtttta  1860
cgattaccgt tcatcgattc tcttgtttgc tccagactct caggcaatga cctgatagcc  1920
tttgtagaga cctctcaaaa atagctaccc tctccggcat gaatttatca gctagaacgg  1980
ttgaatatca tattgatggt gatttgactg tctccggcct ttctcacccg tttgaatctt  2040
tacctacaca ttactcaggc attgcattta aaatatatga gggttctaaa aatttttatc  2100
cttgcgttga aataaaggct tctcccgcaa aagtattaca gggtcataat gtttttggta  2160
caaccgattt agctttatgc tctgaggctt tattgcttaa ttttgctaat tctttgcctt  2220
gcctgtatga tttattggat gttggaattc ctgatgcggt attttctcct tacgcatctg  2280
tgcggtattt cacaccgcat atggtgcact ctcagtacaa tctgctctga tgccgcatag  2340
ttaagccagc cccgacaccc gccaacaccc gctgacgcgc cctgacgggc ttgtctgctc  2400
ccggcatccg cttacagaca agctgtgacc gtctccggga gctgcatgtg tcagaggttt  2460
tcaccgtcat caccgaaacg cgcgagacga aagggcctcg tgatacgcct attttttatag  2520
gttaatgtca tgataataat ggtttcttag acgtcaggtg gcacttttcg gggaaatgtg  2580
cgcggaaccc ctatttgttt attttttctaa atacattcaa atatgtatcc gctcatgaga  2640
caataaccct gataaatgct tcaataatat tgaaaaagga agagtatgag tattcaacat  2700
ttccgtgtcg cccttattcc cttttttgcg gcatttttgcc ttcctgtttt tgctcaccca  2760
gaaacgctgg tgaaagtaaa agatgctgaa gatcagttgg gtgcacgagt gggttacatc  2820
gaactggatc tcaacagcgg taagatcctt gagagttttc gccccgaaga acgttttcca  2880
atgatgagca cttttaaagt tctgctatgt ggcgcggtat tatcccgtat tgacgccggg  2940
caagagcaac tcggtcgccg catacactat tctcagaatg acttggttga gtactcacca  3000
gtcacagaaa agcatcttac ggatggcatg acagtaagag aattatgcag tgctgccata  3060
accatgagtg ataacactgc ggccaactta cttctgacaa cgatcggagg accgaaggag  3120
ctaaccgctt ttttgcacaa catgggggat catgtaactc gccttgatcg ttgggaaccg  3180
gagctgaatg aagccatacc aaacgacgag cgtgacacca cgatgcctgt agcaatggca  3240
acaacgttgc gcaaactatt aactggcgaa ctacttactc tagcttcccg gcaacaatta  3300
atagactgga tggaggcgga taaagttgca ggaccacttc tgcgctcggc ccttccggct  3360
ggctggttta ttgctgataa atctggagcc ggtgagcgtg ggtctcgcgg tatcattgca  3420
gcactggggc cagatggtaa gccctcccgt atcgtagtta tctacacgac ggggagtcag  3480
gcaactatgg atgaacgaaa tagacagatc gctgagatag gtgcctcact gattaagcat  3540
tggtaactgt cagaccaagt ttactcatat atactttaga ttgatttaaa acttcatttt  3600
taatttaaaa ggatctaggt gaagatcctt tttgataatc tcatgaccaa aatcccttaa  3660
cgtgagtttt cgttccactg agcgtcagac cccgtagaaa agatcaaagg atcttcttga  3720
gatccttttt ttctgcgcgt aatctgctgc ttgcaaacaa aaaaaccacc gctaccagcg  3780
gtggtttgtt tgccggatca gagctacca actctttttc cgaaggtaac tggcttcagc  3840
agagcgcaga taccaaatac tgtccttcta gtgtagccgt agttaggcca ccacttcaag  3900
aactctgtag caccgcctac atacctcgct ctgctaatcc tgttaccagt ggctgctgcc  3960
agtggcgata agtcgtgtct taccgggttg gactcaagac gatagttacc ggataaggcg  4020
cagcggtcgg gctgaacggg gggttcgtgc acacagccca gcttggagcg aacgacctac  4080
accgaactga gatacctaca gcgtgagcta tgagaaagcg ccacgcttcc cgaagggaga  4140
aaggcggaca ggtatccggt aagcggcagg gtcggaacag gagagcgcac gagggagctt  4200
ccagggggaa acgcctggta tctttatagt cctgtcgggt ttcgccacct ctgacttgag  4260
cgtcgatttt tgtgatgctc gtcagggggg cggagcctat ggaaaaacgc cagcaacgcg  4320
gccttttac ggttcctggc cttttgctgg ccttttgctc acatgttctt cctgcgtta  4380
tcccctgatt ctgtggataa ccgtattacc gcctttgagt gagctgatac cgctcgccgc  4440
agccgaacga ccgagcgcag cgagtcagtg agcgaggaag cggaagagcg cccaatacgc  4500
aaaccgcctc tccccgcgcg ttggccgatt cattaatgca gcagctgcgc gctcgctcgc  4560
tcactgaggc cgcccgggca aagcccgggc gtcgggcgac ctttggtcgc ccggcctcag  4620
tgagcgagcg agcgcgcaga gagggagtgg ccaactccat cactgggggt tccttgtagt  4680
taatgattaa cccgccatgc tacttatcta cgtagccatg ctctaggaca ttgattattg  4740
actagtggag ttccgcgtta cataacttac ggtaaatggc ccgcctggct gaccgcccaa  4800
cgacccccgc ccattgacgt caataatgac gtatgttccc atagtaacgc caatagggac  4860
tttccattga cgtcaatggg tggagtattt acggtaaact gcccacttgg cagtacatca  4920
agtgtatcat atgccaagta cgccccctat tgacgtcaat gacggtaaat ggcccgcctg  4980
```

```
gcattatgcc cagtacatga ccttatggga ctttcctact tggcagtaca tctacgtatt    5040
agtcatcgct attaccatgg tcgaggtgag ccccacgttc tgcttcactc tccccatctc    5100
ccccccctcc ccaccccaa ttttgtattt atttattttt taattatttt gtgcagcgat    5160
ggggcggg ggggggggg gcgcgcgcca ggcggggcgg ggcggggcga ggggcggggc      5220
ggggcgaggc ggagaggtgc ggcggcagcc aatcagacgc gcgcgctccg aaagtttcct    5280
tttatggcga ggcggcggcg gcggcggccc tataaaaagc gaagcgcgcg gcgggcggga    5340
gtcgctgcgc gctgccttcg ccccgtgccc cgctccgccg ccgcctcgcg ccgcccgccc    5400
cggctctgac tgaccgcgtt actaaaacag gtaagtccgg cctccgcgcc gggttttggc    5460
gcctcccgcg ggcgcccccc tcctcacggc gagcgctgcc acgtcagacg aagggcgcag    5520
cgagcgtcct gatccttccg cccggacgct caggacagcg gcccgctgct cataagactc    5580
ggccttagaa ccccagtatc agcagaagga cattttagga cgggacttgg gtgactctag    5640
ggcactggtt ttctttccag agagcggaac aggcgaggaa aagtagtccc ttctcggcga    5700
ttctgcggag ggatctccgt ggggcggtga acgccgatga tgcctctact aaccatgttc    5760
atgttttctt tttttttcta caggtcctgg gtgacgaaca gggtaccgcc acc           5813

SEQ ID NO: 2               moltype = DNA  length = 526
FEATURE                    Location/Qualifiers
source                     1..526
                           mol_type = other DNA
                           organism = synthetic construct
SEQUENCE: 2
atggccaccg gctctcgcac aagcctgctg ctggctttcg gactgctgtg cctgccttgg    60
ctccaggagg gctccgccgc tagcatcgat accgtcgcta tgtgctggag gcttgctgaa    120
ggctgtatgc tgatagttgc tcatggatct tcgccgtttt ggcctctgac tgacggcgaa    180
gatctgagca actatcagga cacaaggcct gttactagca ctcacatgga acaaatggcc    240
tctagcctgg aggcttgctg aaggctgtat gctgatgtt ctggcatcca tatgcggct      300
ttggcctctg actgacgcgc atatgggcca gaaacatcag gacacaaggc ctgttactag    360
cactcacatg gaacaaatgg cctctagcct ggaggcttgc tgaaggctgt atgctgagaa    420
tttcggtaac gcatccagcg ttttggcctc tgactgacgc tggatgcgac cgaaattctc    480
aggacacaag gcctgttact agcactcaca tggaacaaat ggcctc                    526

SEQ ID NO: 3               moltype = DNA  length = 6339
FEATURE                    Location/Qualifiers
source                     1..6339
                           mol_type = other DNA
                           organism = synthetic construct
SEQUENCE: 3
tctagaataa tcaacctctg gattacaaaa tttgtgaaag attgactggt attcttaact    60
atgttgctcc ttttacgcta tgtggatacg ctgctttaat gcctttgtat catgctattg    120
cttcccgtat ggctttcatt ttctcctcct tgtataaatc ctggttgctg tctctttatg    180
aggagttgtg gcccgttgtc aggcaacgtg gcgtggtgtg cactgtgttt gctgacgcaa    240
cccccactgg ttggggcatt gccaccacct gtcagctcct ttccgggact ttcgctttcc    300
ccctccctat tgccacggcg gaactcatcg ccgcctgcct tgcccgctgc tggacagggg    360
ctcggctgtt gggcactgac aattccgtgg tgttgtcggg gaaatcatcg tccttttcctt    420
ggctgctcgc ctgtgttgcc acctggattc tgcgcgggac gtccttctgc tacgtccctt    480
cggccctcaa tccagcggac cttccttccc gcggcctgct gccggctctg cggcctcttc    540
cgcgtcttcg ccttcgccct cagacgagtc ggatctcctt ttgggccgcc tccccgccta    600
agcttatcga taccgtcgag atctaacttg tttattgcag cttataatgg ttacaaataa    660
agcaatagca tcacaaattt cacaaataaa gcattttttt cactgcattc tagttgtggt    720
ttgtccaaac tcatcaatgt atcttatcat gtctggatct cgacctcgac tagagcatgg    780
ctacgtagat aagtagcatg gcgggttaat cattaactac aaggaacccc tagtgatgga    840
gttggccact ccctctctgc gcgctcgctc gctcactgag gccgggcgac caaaggtcgc    900
ccgacgcccg ggctttgccc gggcggcctc agtgagcgag cgagcgcgca gctggcgtaa    960
tagcgaagag gcccgcaccg atcgcccttc ccaacagttg cgcagcctga atggcgaatg    1020
gcgattccgt tgcaatggct ggcggtaata ttgttctgga tattaccagc aaggccgata    1080
gtttgagttc ttctactcag gcaagtgatg ttattactaa tcaaagaagt attgcgacaa    1140
cggttaattt gcgtgatgga cagactcttt tactcggtgg cctcactgat tataaaaaca    1200
cttctcagga ttctggcgta ccgttcctgt ctaaaatccc tttaatcggc ctcctgttta    1260
gctccccgctc tgattctaac gaggaaagca cgttatacgt gctcgtcaaa gcaaccatag    1320
tacgcgccct gtagcggcgc attaagcgcg gcgggtgtgg tggttacgcg cagcgtgacc    1380
gctacacttg ccagcgccct agcgcccgct cctttcgctt tcttcccttc ctttctcgcc    1440
acgttcgccg gctttccccg tcaagctcta atcggggggc tccctttagg gttccgattt    1500
agtgctttac ggcacctcga ccccaaaaaa cttgattagg gtgatggttc acgtagtggg    1560
ccatcgccct gatagacggt ttttcgccct ttgacgttgg agtccacgtt ctttaatagt    1620
ggactcttgt tccaaactgg aacaacactc aaccctatct cggtctattc ttttgattta    1680
taagggattt tgccgatttc ggcctattgg ttaaaaaatg agctgattta acaaaaattt    1740
aacgcgaatt ttaacaaaat attaacgttt acaatttaaa tatttgctta tacaatcttc    1800
ctgttttgg ggcttttctg attatcaacc ggggtacata tgattgacat gctagtttta    1860
cgattaccgt tcatcgattc tcttgtttgc tccagactct caggcaatga cctgatagcc    1920
tttgtagaga cctctcaaaa atagctaccc tctccggcat gaatttatca gctagaacgg    1980
ttgaatatca tattgatggt gatttgactg tctccggcct ttctcacccg tttgaatctt    2040
tacctacaca ttactcaggc attgcattta aaatatatga gggttctaaa aattttttatc    2100
cttgcgttga aataaaggct tctcccgcaa aagtattaca gggtcataat gtttttggta    2160
caaccgattt atgcctttaa tctgatggtt tattggctaa tcttttgctaat tctttgctt    2220
gcctgatga tttattggat gttggaattc ctgatgcggt attttctcct tacgcatctg    2280
tgcggtattt cacaccgcat atggtgcact ctcagtacaa tctgctctga tgccgcatag    2340
ttaagccagc cccgacaccc gccaacaccc gctgacgcgc cctgacgggc ttgtctgctc    2400
ccggcatccg cttacagaca agctgtgacc gtctccggga gctgcatgtg tcagaggttt    2460
tcaccgtcat caccgaaacg cgcgagacga aagggcctcg tgatacgcct atttttatag    2520
```

-continued

```
gttaatgtca tgataataat ggtttcttag acgtcaggtg gcacttttcg gggaaatgtg  2580
cgcggaaccc ctatttgttt attttttctaa atacattcaa atatgtatcc gctcatgaga  2640
caataaccct gataaatgct tcaataatat tgaaaaagga agagtatgag tattcaacat  2700
ttccgtgtcg cccttattcc ctttttttgcg gcattttgcc ttcctgtttt tgctcaccca  2760
gaaacgctgg tgaaagtaaa agatgctgaa gatcagttgg gtgcacgagt gggttacatc  2820
gaactggatc tcaacagcgg taagatcctt gagagttttc gccccgaaga acgttttcca  2880
atgatgagca cttttaaagt tctgctatgt ggcgcggtat tatcccgtat tgacgccggg  2940
caagagcaac tcggtcgccg catacactat tctcagaatg acttggttga gtactcacca  3000
gtcacagaaa agcatcttac ggatggcatg acagtaagag aattatgcag tgctgccata  3060
accatgagtg ataacactgc ggccaactta cttctgacaa cgatcggagg accgaaggag  3120
ctaaccgctt ttttgcacaa catgggggat catgtaactc gccttgatcg ttgggaaccg  3180
gagctgaatg aagccatacc aaacgacgag cgtgacacca cgatgcctgt agcaatggca  3240
acaacgttgc gcaaactatt aactggcgaa ctacttactc tagcttcccg gcaacaatta  3300
atagactgga tggaggcgga taaagttgca ggaccacttc tgcgctcggc ccttccggct  3360
ggctggttta ttgctgataa atctggagcc ggtgagcgtg ggtctcgcgg tatcattgca  3420
gcactggggc cagatggtaa gccctcccgt atcgtagtta tctacacgac ggggagtcag  3480
gcaactatgg atgaacgaaa tagacagatc gctgagatag gtgcctcact gattaagcat  3540
tggtaactgt cagaccaagt ttactcatat atactttaga ttgatttaaa acttcatttt  3600
taatttaaaa ggatctaggt gaagatcctt tttgataatc tcatgaccaa aatcccttaa  3660
cgtgagtttt cgttccactg agcgtcagac cccgtagaaa agatcaaagg atcttcttga  3720
gatccttttt ttctgcgcgt aatctgctgc ttgcaaacaa aaaaaccacc gctaccagcg  3780
gtggtttgtt tgccggatca agagctacca actctttttc cgaaggtaac tggcttcagc  3840
agagcgcaga taccaaatac tgtccttcta gtgtagccgt agttaggcca ccacttcaag  3900
aactctgtag caccgcctac atacctcgct ctgctaatcc tgttaccagt ggctgctgcc  3960
agtggcgata agtcgtgtct taccgggttg gactcaagac gatagttacc ggataaggcg  4020
cagcggtcgg gctgaacggg gggttcgtgc acacagccca gcttggagcg aacgacctac  4080
accgaactga gatacctaca gcgtgagcta tgagaaagcg ccacgcttcc cgaagggaga  4140
aaggcggaca ggtatccggt aagcggcagg gtcggaacag gagagcgcac gagggagctt  4200
ccaggggaa acgcctggta tctttatagt cctgtcgggt ttcgccacct ctgacttgag  4260
cgtcgatttt tgtgatgctc gtcagggggg cggagcctat ggaaaaacgc cagcaacgcg  4320
gcctttttac ggttcctggc cttttgctgg ccttttgctc acatgttctt tcctgcgtta  4380
tcccctgatt ctgtggataa ccgtattacc gcctttgagt gagctgatac cgctcgccgc  4440
agccgaacga ccgagcgcag cgagtcagtg agcgaggaag cggaagagcg cccaatacgc  4500
aaaccgcctc tccccgcgcg ttggccgatt cattaatgca gcagctgcgc gctcgctcgc  4560
tcactgaggc cgcccgggca aagcccgggc gtcgggcgac ctttggtcgc ccggcctcag  4620
tgagcgagcg agcgcgcaga gagggagtgg ccaactccat cactaggggt tccttgtagt  4680
taatgattaa cccgccatgc tacttatcta cgtagccatg ctctaggaca ttgattattg  4740
actagtggag ttccgcgtta cataacttac ggtaaatggc ccgcctggct gaccgcccaa  4800
cgacccccgc ccattgacgt caataatgac gtatgttccc atagtaacgc caatagggac  4860
tttccattga cgtcaatggg tggagtattt acggtaaact gcccacttgg cagtacatca  4920
agtgtatcat atgccaagta cgccccctat tgacgtcaat gacggtaaat ggcccgcctg  4980
gcattatgcc cagtacatga ccttatggga ctttcctact tggcagtaca tctacgtatt  5040
agtcatcgct attaccatgg tcgaggtgag ccccacgttc tgcttcactc tccccatctc  5100
ccccccctcc ccacccccaa ttttgtattt atttattttt taattatttt gtgcagcgat  5160
ggggcgggg ggggggggg gcgcgcgcca ggcggggcgg ggcggggcga ggggcggggc  5220
ggggcgaggc ggagaggtgc ggcggcagcc aatcagagcg gcgcgctccg aaagtttcct  5280
tttatggcga ggcggcggcg gcggccagcg tataaaaagc gaagcgcgcg gcgggcggga  5340
gtcgctgcgc gctgccttcg ccccgtgccc cgctccgccg ccgcctcgcg ccgcccgccc  5400
cggctctgac tgaccgcgtt actaaaacag gtaagtccgg cctccgcgcc gggtttttggc  5460
gcctcccgcg ggcgcccccc tcctcacggc gagcgctgcc acgtcagacg aagggcgcag  5520
cgagcgtcct gatccttccg cccggacgct caggacagcg gcccgctgct cataagactc  5580
ggccttagaa ccccagtatc agcagaagga cattttagga cgggacttgg gtgactctag  5640
ggcactggtt ttctttccag agagcggaac aggcgaggaa aagtagtccc ttctcggcga  5700
ttctgcggag ggatctccgt ggggcggtga acgccgatga tgcctctact aaccatgttc  5760
atgttttctt ttttttttcta caggtcctgg gtgacgaaca gggtaccgcc accatggcca  5820
ccggctctcg cacaagcctg ctgctggctt tcggactgct gtgcctgcct tggctccagg  5880
agggctccgc cgctagcatc gataccgtcg ctatgtgctg gaggcttgct gaaggctgta  5940
tgctgatagt tgctcatgga tcttcgccgt tttggcctct gactgacggc gaagatctga  6000
gcaactatca ggacacaagg cctgttacta gcactatcac ggaacaaatg gcctctagcc  6060
tggaggcttg ctgaaggctg tatgctgatg tttctggcat ccatatgcgc gtttttgcct  6120
ctgactgacg cgcatatggg ccagaaacat caggacacaa ggcctgttac tagcactcac  6180
atggaacaaa tggcctctag cctggaggct tgctgaaggc tgtatgctga gaatttcggt  6240
aacgcatcca gcgttttggc ctctgactga cgctggatgc gaccgaaatt ctcaggacac  6300
aaggcctgtt actagcactc acatggaaca aatggcctc                          6339
```